United States Patent [19]

Awolin

[11] Patent Number: 5,752,947
[45] Date of Patent: May 19, 1998

US005752947A

[54] MULTIPLE FOLDED SIDE BARRIER FOR IMPROVED LEAKAGE PROTECTION

[75] Inventor: Bernhard Awolin, Rammsee, Germany

[73] Assignee: McNeil-PPC, Inc., Skillman, N.J.

[21] Appl. No.: 782,857

[22] Filed: Jan. 13, 1997

Related U.S. Application Data

[63] Continuation of Ser. No. 415,808, Apr. 3, 1995, abandoned.
[51] Int. Cl.[6] .................................................. A61F 13/15
[52] U.S. Cl. .................................... 604/387; 604/385.1
[58] Field of Search ............................ 604/358, 369–370, 604/378, 385.1, 385.2, 387

[56] References Cited

FOREIGN PATENT DOCUMENTS 2266225  10/1993  United Kingdom ............... 604/385.1

Primary Examiner—Robert A. Clarke
Attorney, Agent, or Firm—James P. Barr

[57] ABSTRACT

An absorbent product having fluid repellent leakage barriers is provided to reduce or prevent side leakage. The leakage barriers comprise folded structures which are attached longitudinally on the body-facing side of the absorbent product adjacent each lateral edge of the absorbent product and the distal ends of each leakage barrier are anchored to the absorbent product. When the absorbent product is flexed concavely along its longitudinal axis with respect to the body-facing side the leakage barriers at least partially open to form upstanding walls.

26 Claims, 3 Drawing Sheets

MULTIPLE FOLDED SIDE BARRIER FOR IMPROVED LEAKAGE PROTECTION

This is a continuation, of application Ser. No. 08/415,808, filed Apr. 3, 1995 now abandoned.

FIELD OF THE INVENTION

The present invention relates to absorbent products and, more particularly, to disposable absorbent products having improved side leakage protection.

BACKGROUND OF THE INVENTION

Absorbent products such as sanitary napkins, panty liners, diapers, and incontinence products and the like have a fluid pervious body-facing side through which liquid discharge is absorbed and a fluid impervious garment-facing side which protects the garment worn by the wearer of the absorbent product from becoming wet and/or stained. These absorbent products are essentially longitudinally shaped, i.e., having a narrower distance between the lateral edges than the distance between the longitudinal ends so that the absorbent product can be comfortably disposed between the wearer's legs and cover the perineal area.

A common problem associated with such products is side leakage. One cause of side leakage is due to misalignment of the absorbent product caused by shifting while the product is worn. Efforts to eliminate or reduce misalignment generally involve the use of adhesives and or side flaps having adhesives to adhere the absorbent product to a wearer's undergarment. However, if the wearer misaligns the absorbent product with respect to the undergarment or if the absorbent product slips while being worn, an improper alignment between the centerline of the absorbent product and the vaginal opening will accelerate side leakage.

Side leakage can also occur due to bunching which occurs when the absorbent product is subjected to compressive forces from the wearer's thighs which tends to decrease the lateral width of the absorbent area disposed between the wearer's legs. The tendency of a product to bunch usually increases as the absorbent product becomes saturated thereby further reducing the lateral width of the absorbent area and also deforming the contour of the absorbent product. Such deformation and reduction in the lateral width of the absorbent area often results in side leakage.

To combat these problems, many attempts have been made to reduce side leakage in various absorbent products. For example, C-folds or multiple C-folds are known in which an internal layer of absorbent material is folded at the edges to increase the thickness of the absorbent product at its lateral edges. A sanitary napkin having such folds is disclosed in U.S. Pat. No. 3,699,966 (Chapuis). Diapers having C-folds or multiple C-folds are disclosed in U.S. Pat. No. 3,744,494 (Marsan); U.S. Pat. No. 3,995,640 (Schaar); U.S. Pat. Nos. 4,040,423 and 4,041,950 (Jones, Sr.); U.S. Pat. No. 4,610,679 (Matsushita); and U.S. Pat. No. 3,863,637 (MacDonald et al). An adult incontinence product having a C-fold is disclosed in U.S. Pat. 3,068,798 (Hokanson). Unfortunately, side leakage still persists when these products are used due to misalignment and bunching.

Other attempts to combat side leakage involve covering the C-folds or multiple C-folds with an impervious barrier sheet to create a more centralized channel along the longitudinal axis of the absorbent product. Diapers having such covered C-folds are disclosed in U.S. Pat. No. 5,263,949 (Karami et al) and U.S. Pat. No. 3,920,017 (Karami). Since the channel in these diapers deforms when bunching occurs, side leakage remains a problem.

Other efforts to reduce side leakage associated with absorbent products include embossing or channeling techniques. For example, U.S. Pat. No. 4,655,759 (Romans-Hess et al) discloses a sanitary napkin having embossed channels disposed adjacent to the longitudinal edges of the napkin. The channels allow the sides of the napkin to fold upward to prevent side leakage. Unfortunately, bunching and particularly misalignment reduce the effectiveness of this sanitary napkin.

The use of upstanding structures formed by securing an elastic strip along the side edges of a napkin are also known to reduce side leakage as disclosed for example in U.S. Pat. No. 4,944,735 (Mokry), and U.S. Pat. No. 5,074,856 (Coe et al.). U.S. Pat. No. 5,074,856 further discloses the use of a plastic foam shell molded into a gathered wall and then covered with a liner and having an elastic strip between layers of the napkin. Unfortunately, elastics and molded plastics are relatively expensive for use in disposable absorbent products. Moreover, these upstanding structures are provided only on a central portion of the napkin thus misalignment or slippage or the napkin permits side leakage near the ends of the napkin.

Therefore, there exists a need for an absorbent product having improved side leakage protection against misalignment, slippage and bunching which does not require elastic components or foam materials.

SUMMARY OF THE INVENTION

It is an object of the present invention to provide a novel, absorbent product having improved side leakage protection.

In accordance with the present invention, there has been provided an absorbent product having a fluid impervious garment facing side and a fluid pervious body facing side, a first lateral edge and a second lateral edge, and a first folded structure attached adjacent to the first lateral edge which provides a first leakage barrier and a second folded structure attached adjacent to the second lateral edge which provides a second leakage barrier so that the first and second leakage barriers form upstanding walls when the absorbent product is flexed concavely along its longitudinal axis with respect to the fluid pervious body facing side.

Also provided in accordance with the present invention is a sanitary napkin comprising a fluid pervious topsheet, a fluid impervious bottom sheet, an absorbent core interposed between the topsheet and the bottom sheet, and first and second lateral edges, and having:

- a first longitudinally shaped folded structure attached adjacent the first lateral edge to provide a first leakage barrier;
- a second longitudinally shaped folded structure attached adjacent the second lateral edge to provide a second lateral edge; and
- the first and second leakage barriers forming upstanding walls when the sanitary napkin is flexed concavely with respect to the absorbent side.

Also provided in accordance with the present invention is a method of producing an absorbent product having an improved side leakage capability, comprising the steps of:

- forming a first leakage barrier having multiple pleated folds from a sheet of material;
- attaching the first leakage barrier adjacent a first lateral edge of the absorbent product;
- forming a second leakage barrier having multiple pleated folds from a sheet of material; and
- attaching the second leakage barrier adjacent a second lateral edge of the absorbent product.

BRIEF DESCRIPTION OF THE DRAWINGS

The present invention will be better understood, and its numerous objects and advantages will become apparent by reference to the following detailed description of the invention when taken in conjunction with the following drawings, in which.

DETAILED DESCRIPTION OF THE INVENTION

Figure 1:
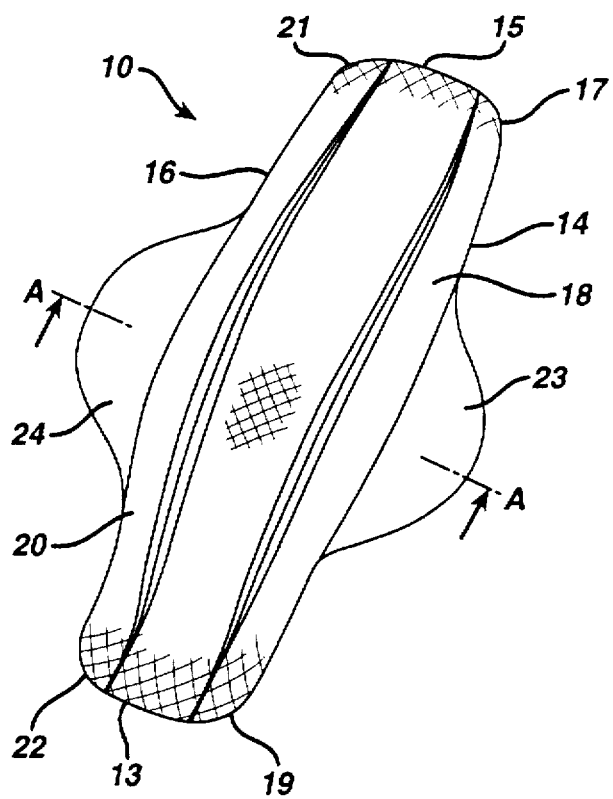
FIG. 1 show a perspective view of a sanitary napkin having improved side leakage protection according to one embodiment of the invention.

The present invention is directed to a novel absorbent product having improved side leakage protection, and more particularly to an absorbent product having a fluid impervious garment facing layer, a fluid pervious body facing layer and an absorbent core between the garment facing layer and the body facing layer, first and second lateral edges, a first folded structure comprising a first leakage barrier having a longitudinal shape and attached longitudinally adjacent to the first lateral edge and proximate to a region of the absorbent product which is flexed concavely in the longitudinal direction along the longitudinal axis of the absorbent product to substantially conform to the shape of the perineal area of the wearer and a second folded structure comprising a second leakage barrier having a longitudinal shape and attached longitudinally adjacent to the second lateral edge which is substantially opposite to the first lateral edge so that the first and second leakage barriers at least partially unfold to form upstanding walls which extend into the creases at the sides of the female genital organs when the absorbent product is flexed concavely with respect to the body facing side.

The leakage barriers generally comprise a flexible sheet material having multiple folds forming longitudinally shaped pleated cuffs which are capable of at least partially unfolding to form the upstanding walls in an area which is substantially proximate to a central region of the absorbent product and which are thus effective for either inhibiting side leakage associated with absorbent products or for slowing the transfer rate of a fluid across the leakage barrier. The leakage barriers of the present invention should be attached or secured to the absorbent product such that the top layer of the pleated leakage barrier structure is higher, i.e., closer to the body surface of the wearer, than the surface to which it is attached, and is preferably at least as high as the top of the absorbent core and is most preferably higher than the top of the absorbent core. That is, the leakage barriers, to be effective, must preferentially contact the body of the wearer rather than the surfaces to which they are attached to thus form an effective "gasket" or "seal" along the lateral sides of the central absorbent core of the absorbent product. A preferred method for attaching the leakage barriers to the absorbent product is in a generally parallel relationship to one another, on opposite lateral sides from each other and secured longitudinally adjacent the lateral edges of the absorbent product. The leakage barriers are generally attached to the absorbent product on the fluid permeable body facing layer of the absorbent product, to a body-facing side of side flanges which may be present on an absorbent product, to a body-facing side of wings or tabs which may be present on an absorbent product as well as to areas which are proximate to any two of the foregoing areas.

The leakage barriers may be attached or secured to the absorbent product using any conventional techniques which are used for securing or adhering flexible materials together including, but not limited to the use of, adhesives, heat sealing techniques, ultrasonic bonding techniques, cold flow techniques, mechanical crimping, and the like, and any combination thereof. The mode of attachment can be continuous or discontinuous, provided, of course, that the bottom most layer is substantially secured along its longitudinal axis to a surface of the absorbent product to substantially impede the transference of fluid across the leakage barrier. Preferably, the bottom-most layer of the leakage barrier is attached continuously using an adhesive or heat bonding, adjacent to the longitudinal axis of the absorbent product. The leakage barriers of this invention will open, at least partially, to form upstanding walls when the absorbent product is flexed concavely toward the body, by virtue of their pleated or folded design and by the manner in which they are attached to the absorbent product. That is, it is considered important that the leakage barriers of this invention have both the pleated design features as well as a particular mode of attachment, wherein the bottom-most layer of the leakage barrier is secured to the body-facing side of the absorbent product in a region of the absorbent product which will be flexed concavely by the wearer of the absorbent product and wherein at least one area of each pleated layer of the leakage barrier, preferably the distal ends of each pleated layer of the leakage barriers are adhered to each other. The bottom-most layer of each leakage barrier may be secured to the absorbent product having its fold-crease with the next layer of the leakage barrier, facing either inwardly or outwardly with respect to the center of the absorbent product. Preferably, the bottom-most layer is attached using an adhesive, adjacent and parallel to a longitudinal axis of the absorbent product and the distal ends of all of layers of the pleated folds are anchored together and onto the absorbent product.

The leakage barriers of the present invention may be formed by folding a suitable sheet material in an alternating "Z-fold" pattern multiple times to form a plurality of pleated folds. The fold creases between the layers that define the pleats may range from sharp creases to a soft radii of curvature, provided, of course, that one layer changes direction with respect to its neighboring layer. In a preferred embodiment the sheet is folded from one to six times. In a more preferred embodiment the sheet is folded from two to four times. Folding of the sheet material to form the leakage barrier may be done before or after it is attached to the sanitary napkin.

The length of the leakage barriers is not, per se, critical to the invention, provided of course, that the length is sufficient to span the area of fluid discharge within the concavely flexed region of the absorbent product. Generally, this length is at least about one third of the length of a conventional, substantially symmetrical absorbent product, and is preferably between one third and substantially equal to the length of the absorbent product. Non-symmetrically shaped absorbent products are known in the art, and generally provide elongated absorbent portions to cover the buttocks area of the wearer of the absorbent product. In these absorbent products, the length of the liquid barrier can range from substantially less than one-third of the length of the absorbent product to a length which is substantially equal to the length of the absorbent product. Preferably, the leakage barriers have a length in a range between one third of the entire length of the absorbent product to substantially equal to the length of the absorbent product.

The leakage barriers may be formed either from single sheets or from multiple-ply laminates of flexible materials which are capable of being folded into a pleated structure and are preferably formed from hydrophobic, fluid repellent, air permeable materials such as nonwovens, apertured plastic films, foams or combinations of these materials. While the use of hydrophobic material is preferred, the leakage barriers may also be formed of materials that are not all necessarily hydrophobic, fluid repellent or air permeable, provided, of course, that the materials substantially impede the transference of fluid across the leakage barrier when secured to the absorbent product. Specific examples of suitable materials include, but are not limited to, thermally bonded nonwovens made of fibers such as polypropylene, polyester, nylon, or of bicomponent fibers having a high melting point internal polymeric component that retains the fiber structure during thermal bonding and a lower melting point external polymeric component that melts during thermal bonding to fuse the fibers together to form the web. Examples of bicomponent fibers having such high and low melting point polymer components are well known and include, for example, polyester and polyethylene, polypropylene and polyethylene and high and low melting polyesters, respectively. Other suitable thermally bonded nonwoven fabrics include spunbond, meltblown, thermally calendered, thermally embossed and hot air bonded nonwoven fabrics. Hydrophobic, fluid repellent nonwoven fabrics bonded with chemical binders can also be used, as well as nonwoven fabrics made by hydraulic aperturing, needle punching, etc. Other suitable materials include, finely apertured plastic films, reticulated and non-reticulated foams, and breathable non-apertured films such as those made of nylon, polyester or polyurethane, and may, but need not, be made, completely or in part, of inherently elastic materials, or have elastic components such as elastic threads or tapes that may or may not be pretensioned to achieve curvature to the absorbent product or to help the walls of the leakage barriers stand up. These elastic components may be secured to one or more layers of the leakage barriers, and may be secured by any conventional techniques including adhesives, heat bonding, ultrasonic bonding, stitching, etc. In a particularly preferred embodiment, at least one elastic component is included between the layers of laminates of hydrophobic, fluid repellant, air permeable materials and is most preferably laminated into the top layer of the pleated leakage barrier. The leakage barriers may also be extensions of the materials comprising the body facing side of the absorbent product, the garment facing side of the absorbent product or a combination of the two.

When the leakage barriers of the present invention are formed from multiple-ply laminates of the above-described flexible sheet materials, these multiple-ply laminates may comprise as many as five plies, and preferably comprise less than four plies. A convenient way to achieve a multiple-ply laminate is to fold a flexible sheet material on itself at least one or more times; and then to fold the multiple-ply laminate sheet to form a pleated leakage barrier. Other ways of forming multiple ply laminated structures are known in the art and include such techniques as layering, laminating and the like.

It should be understood that when using a multiple-ply laminated sheet of material, each ply may be comprised of the same or different sheet materials. Thus, an absorbent material may be folded together with a hydrophobic fluid repellant material to provide a leakage barrier which forms an inner absorbent lining so that side leakage may be absorbed by the absorbent lining while the hydrophobic material provides an outer fluid barrier. Thus in an alternative embodiment, the leakage barrier may comprise a multiple-ply sheet having both absorbent and hydrophobic materials, folded to form a pleated structure capable of at least partially opening when attached to the body-facing side of an absorbent product when the sanitary napkin is flexed concavely with respect to the body-facing side. Suitable absorbent materials include materials which are used in absorbent product cover layers, transfer layers, absorbent core materials, and combinations thereof.

In yet another embodiment of this invention, the leakage barriers may be formed from a flexible polymeric foam material which has been folded or optionally extruded into a pre-formed pleated structure. A typical example of a flexible polymeric foam which is suitable for forming these pleated structures is polyethylene foam. Polyethylene foams have heretofore been used to form liquid impermeable backing layers in sanitary napkins. Thus, in an optional embodiment, the lateral edges of a polyethylene foam backing layer of a sanitary napkin can be folded a plurality of times to form pleated leakage barriers along the lateral edges of the sanitary napkin.

In an additional embodiment of this invention, the absorbent product contains an internal layer of an absorbent pad having at least one C-fold formed on opposite lateral edges thereof to provide additional absorbent and barrier thickness along the sides of the absorbent product thereby providing an additional source of side leakage protection. Additionally, or alternatively, the absorbent pad may be embossed to form densified regions which guide fluid within the absorbent pad and minimize the fluid's escape from the absorbent pad. Such embossed or densified regions may also be part of the fold region of the C-fold.

Also provided in accordance with the present invention is an absorbent product in the form of a sanitary napkin having the above described leakage barriers and optionally possessing the above described alternate embodiments. The sanitary napkins of this invention comprise a first folded structure having a longitudinal shape which is attached longitudinally adjacent a first lateral edge of the napkin, providing a first leakage barrier and a second folded structure having a longitudinal shape attached longitudinally adjacent the second lateral edge of the napkin providing a second leakage barrier.

The sanitary napkin according to the invention is preferably produced by forming a first leakage barrier having multiple pleated folds from a sheet of hydrophobic material, and attaching the bottom-most layer of the first leakage barrier adjacent a first edge of the sanitary napkin, forming a second leakage barrier having multiple pleated folds from a sheet of hydrophobic material, and attaching the bottom-most layer of the second leakage barrier adjacent a second edge of the sanitary napkin.

More preferably, the bottom-most layer of the leakage barrier is attached, along its longitudinal axis to the lateral edge of the sanitary napkin and the distal ends of all of layers of the pleated leakage barriers are secured together and onto the sanitary napkin product. The leakage barriers may be attached to the sanitary napkin using any of the above-discussed techniques and is preferably attached by using an adhesive or by use of heat sealing. The leakage barriers may also be extensions of the material comprising the body facing side of the sanitary napkin, the garment facing side of the sanitary napkin or a laminated combination of the body facing material and the garment facing material.

The sanitary napkins of this invention are generally longitudinally shaped and may have substantially straight, parallel lateral sides, or may preferably have an hour-glass or dog bone shape wherein the lateral edges are in a curved, arcuate shape. Preferred sanitary napkins also have wings or tabs along their lateral edges, which may or may not have adhesive means for securing the tabs to each other or to the undergarment of the wearer.

Preferred embodiments of the invention are shown in FIGS. 1–6 wherein like reference numerals refer to like elements in the drawings. FIG. 1 shows a sanitary napkin 10 having improved leakage protection according to the invention. The sanitary napkin 10 having a generally elongated shape is shown with a first lateral edge 14 and a second lateral edge 16 and longitudinal ends 13 and 15. A first leakage barrier 18 is attached on to sanitary napkin 10 adjacent the first lateral edge 14 and a second leakage barrier 20 is attached to the sanitary napkin 10 adjacent the second lateral edge 16. A first tab 23 may extend from the first lateral edge and a second tab 24 may extend from the second lateral edge. It should be understood that the term "tab" as used herein includes wings, flaps or any generally flexible or hinged structures extending from the edges of the napkin and used to secure the napkin to the wearer's undergarment. It should be further understood that while tabs are provided in a preferred embodiment of the invention, tabs are not essential to the invention.

The leakage barriers 18, 20 preferably comprise a unitary sheet of substantially hydrophobic material folded multiple times to form a pleated cuff. In this preferred embodiment, the distal ends 17,21 of respective first and second leakage barriers 18, 20 are anchored proximate to longitudinal end 15 of the sanitary napkin. Similarly, distal ends 19, 22 of respective first and second leakage barriers 18, 20 are anchored proximate to longitudinal end 13 of the sanitary napkin. As shown in FIG. 1, the length of the leakage barriers is substantially the same as the length of the sanitary napkin.

Figure 2:
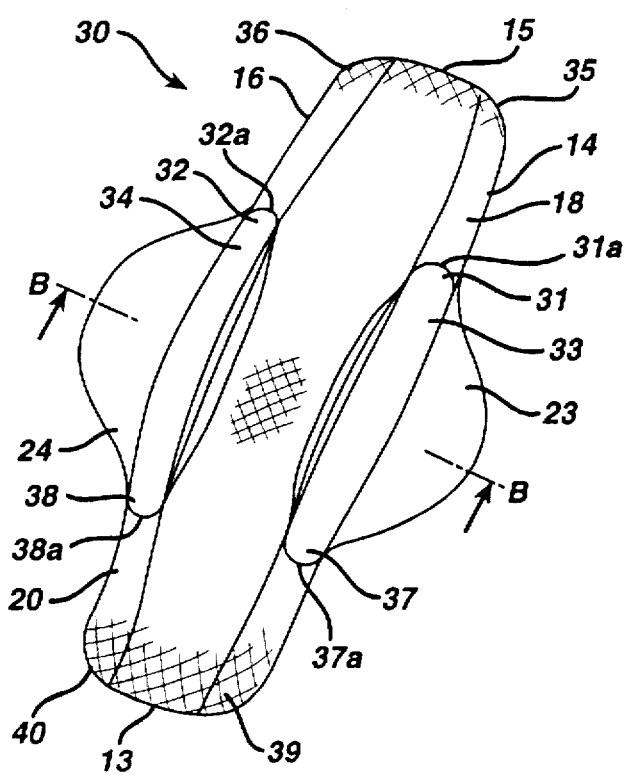
FIG. 2 shows a perspective view of an absorbent product having improved side leakage protection according to another embodiment of the invention.

FIG. 2 shows another preferred embodiment of this invention in the form of a sanitary napkin 30 having the same general features and most of the specific features of the sanitary napkin 10 shown in FIG. 1. However, in this preferred embodiment, distal ends 31, 32 of respective first and second leakage barriers 33,34 are anchored proximate points, that are about one third the longitudinal dimension of sanitary napkin 30, measured inwardly of longitudinal ends 35,36 of sanitary napkin 30. Similarly, distal ends 37,38 of respective first and second leakage barriers 33,34 are anchored proximate points, that are about one third the longitudinal dimension of sanitary napkin 30, measured inwardly of longitudinal ends 39,40 of sanitary napkin 30. Thus in FIG. 2, leakage barrier 33 is located along the middle third of lateral edge 14 of sanitary napkin 30, the bottom-most layer of leakage barrier 33 being attached to body facing side 18 along lateral edge 14 of sanitary napkin 30, and the distal ends 31,37 of leakage barrier 33 being anchored to body facing side 18 at regions 31,37 proximate distal ends 31,37. Equivalently, leakage barrier 34 is located along the middle third of lateral edge 16 of sanitary napkin 30, the bottom-most layer of leakage barrier 33 being attached to body facing side 20 at regions 32,38 proximate distal ends 32,38. Optionally, leakage barriers 33,34 in FIG. 2 need not be located along the middle third of lateral edges 16,18 of sanitary napkin 30. They can be located and attached anywhere along the lateral edges, for example, from distal end 35 to region 37 for one leakage barrier and from distal end 36 to region 38 for the other leakage barrier. Such an arrangement is particularly useful for night usage when the sanitary napkin is worn with the leakage barriers positioned toward the back of the body.

Figure 3:
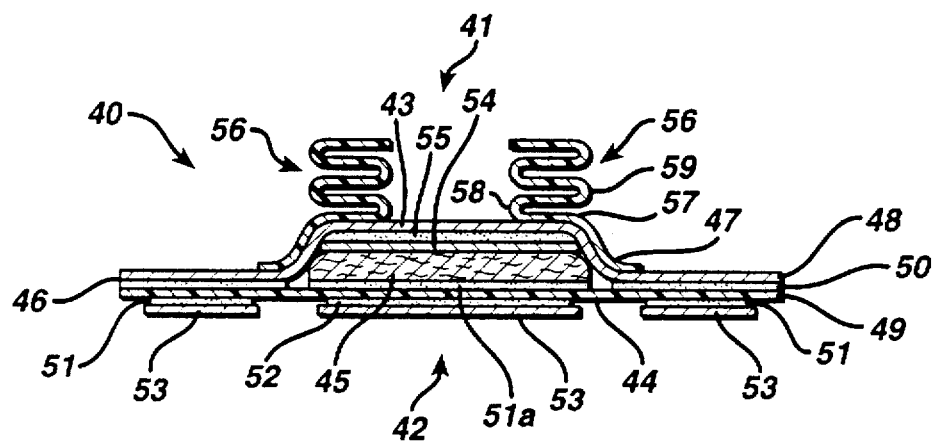
FIGS. 3 shows a cross section of one embodiment of the sanitary napkin of this invention shown in FIG. 1 taken on line A—A or line B—B respectively.
Figure 4:
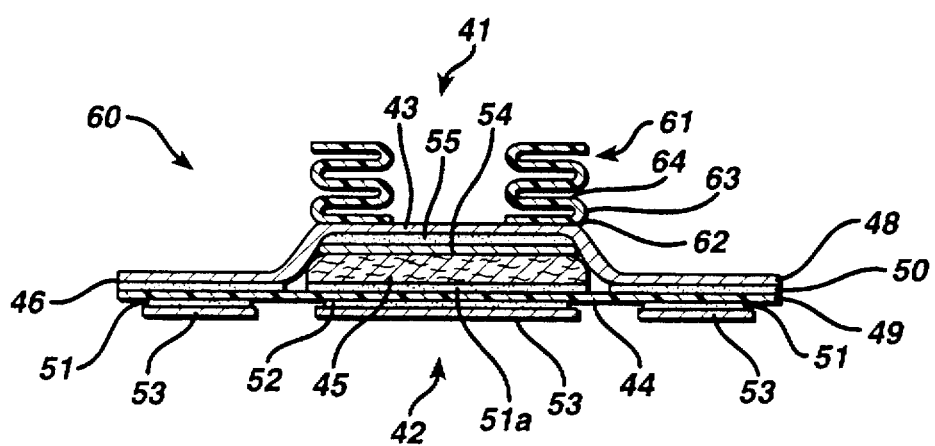
FIG. 4 shows a cross section of an alternative embodiment of the sanitary napkin of this invention shown in FIG. 2 taken on line A—A or line B—B respectively.

FIGS. 3 and 4 show cross sections of the sanitary napkin taken either on line A—A in FIG. 1 or on line B—B in FIG. 2. Sanitary napkin 40 in FIG. 3 and sanitary napkin 60 in FIG. 4 each have a body facing side 41, a garment facing side 42, a perforate cover 43, an impervious barrier sheet 44 and an absorbent core 45. The absorbent core 45 is confined between the barrier sheet 44 and perforate cover 43 by using heat, adhesive or mechanical crimping to seal barrier sheet 44 to the perforate cover 43. In a preferred embodiment, the distal ends of the leakage barriers are sealed to the cover in the process of sealing the absorbent core between the barrier sheet and perforate cover. The absorbent core may comprise C-folds or multiple C-folds to provide additional sources of the leakage reduction.

Additionally, there may be tabs 46 extending from each lateral edge 47, the tabs 46 being comprised of an extension 48 of perforate cover 43 attached to an extension 49 of barrier sheet 44 with adhesive means 50. Adhesive means 51,52 are also applied to the barrier side of tabs 46 and to the barrier side of the sanitary napkin for attachment to a garment, adhesive means 51,52 being protected until use by release sheets 53. Also additionally, absorbent core 45 may be attached by adhesive means 51a to barrier sheet 44. A fluid transfer layer 54 may be applied to the body facing side of absorbent core 45, the body facing side of fluid transfer layer 54 being attached to perforate cover 43 with a fluid permeable adhesive means 55.

Absorbent core 45 can be any absorbent material which is capable of absorbing bodily exudate such as menses, blood, urine, etc., and generally includes wood fluff, wet or dry crosslinked wood fluff, rayon or cotton, tissue, synthetic fibers, sphagnum moss, meltblown polymers and superabsorbent fibers or particles and combinations thereof, the combinations being represented by homogeneous mixtures, inhomogeneous mixtures, absorbent concentration gradient mixtures, density gradient mixtures and laminates and layers thereof.

Transfer layer 54, usually of lower density and thereby of higher porosity than a substantial portion of absorbent core 45, may be comprised of nonwovens containing hydrophilic fibers, hydrophobic fibers, crimped fibers, curly fibers, grooved fibers, capillary containing fibers and mixtures thereof, the fibers being loosely confined or being bonded to each other to some degree by means or combinations of means such as chemical binder means, mechanical means such as needle punching or hydroentangling, thermal means such as spunbonding, meltblowing, through-air blowing, calendaring, embossing and the like.

Perforate cover 43 may be comprised of nonwoven fabrics, films or combinations thereof, where the perforations may be of different sizes and shapes and may be two or three dimensional, with the three dimensional perforations being of uniform, tapering or varying diameters and tortuosities, as one proceeds in the perforations from one facing side of the perforate cover to the opposite facing side.

Barrier sheet 44 may be comprised of polymers such as polyethylene, polypropylene, other polyolefins, polyesters, polyurethanes and polyamides, to form sheets that are impervious to liquids and to gases. However, they may also be pervious to gases, to yield what are known as breatheable films.

Each leakage barrier 56 of the two shown in FIG. 3 is attached with its bottom-most layer 57 having a fold crease 58 with the next layer 59 of leakage barrier 56, the fold crease 58 facing inwardly toward the center of sanitary napkin 40.

In FIG. 4, each leakage barrier 61 of the two shown, is attached with its bottom-most layer having a fold-crease 63 with the next layer 64 of leakage barrier 65, the fold-crease 63 facing outwardly from the center of sanitary napkin 60.

Figure 5:
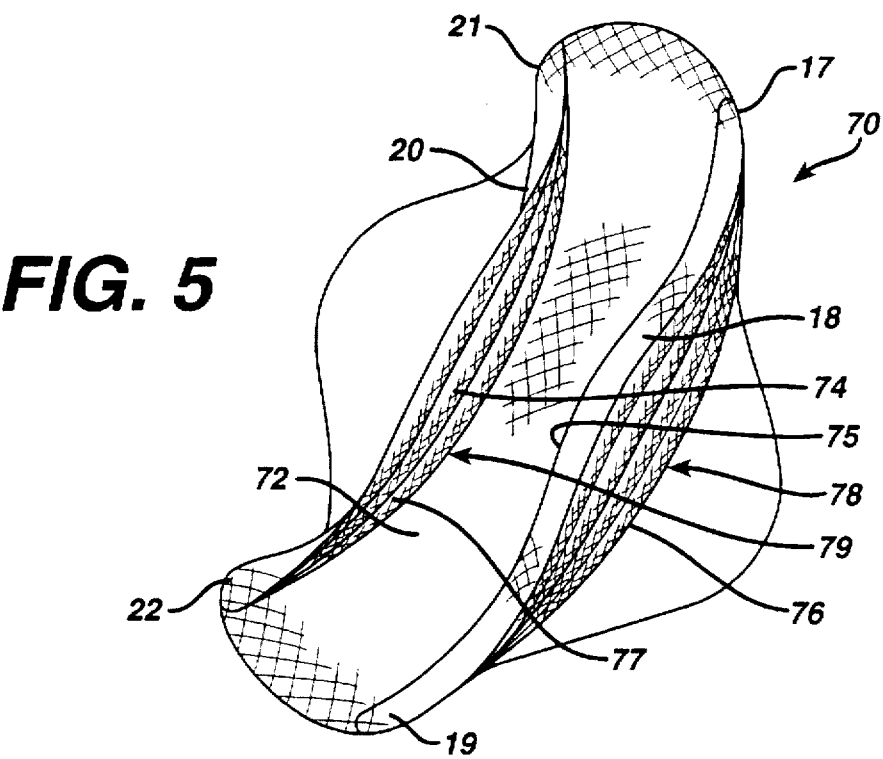
FIG. 5 shows a perspective view of the sanitary napkin of FIG. 2 flexed concavely with respect to the body facing side of the sanitary napkin.

The function of the leakage barriers according to the invention, to reduce side leakage, can be explained with reference to FIGS. 5 and 6. FIG. 5 shows the sanitary napkin 70 according to a preferred embodiment, shown in FIG. 1, flexed concavely with respect to body-facing side 72 of the sanitary napkin 70. The folded structure of leakage barriers 18 and 20 partially unfold to form upstanding walls 75 on body facing side 72 of sanitary napkin 70. The mechanism which operates to at least partially unfold the leakage barriers is provided by a combination of features of the invention. These features include adhering the length of bottom-most layers 76,77 of the pleated cuff to the sanitary napkin, anchoring entirely the distal ends 17,19,21,22 of the leakage barrier strip to the sanitary napkin, and providing leakage barriers 78,79.

The upstanding walls 74 are preferably unrestrained over the length of the sanitary napkin to provide a substantially complete barrier to fluid along the entire length of the sanitary napkin. Since the upstanding walls are formed by concavely flexing the sanitary napkin, thereby providing the longitudinal compression to spread open the accordion pleated cuffs, the effectiveness of the leakage barriers is not significantly affected by bunching, misalignment, or slippage. The hydrophobic material of the leakage barriers provides a significant degree of comfort to the wearer being soft and not easily wetter. Foam-like materials are not required to supply stiffening or cushioning. Elastic components are not required to raise the pleated cuffs and keep them in an upstanding condition.

Figure 6:
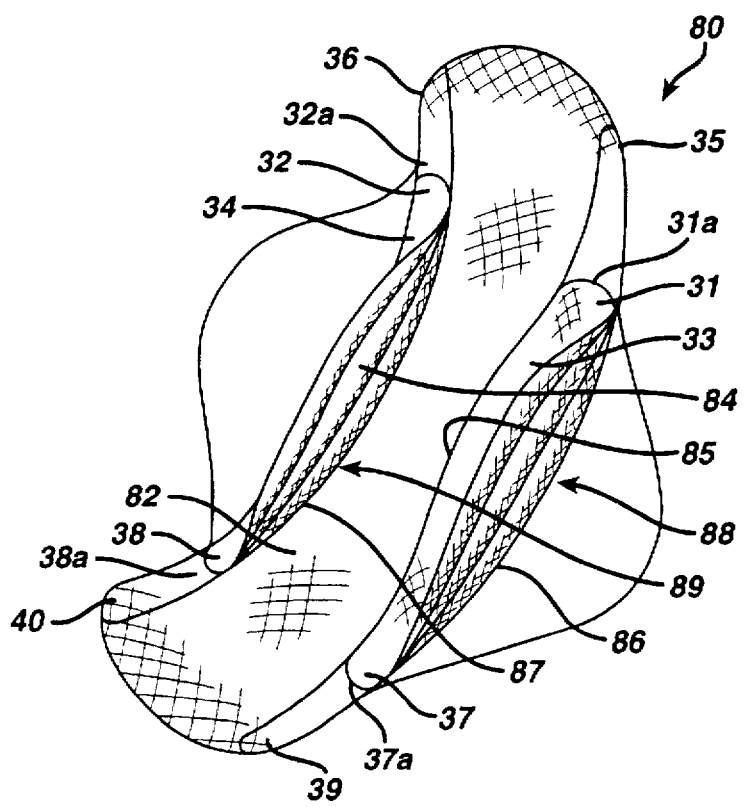
FIG. 6 shows a perspective view of the sanitary napkin of FIG. 1 flexed concavely with respect to the body facing side of the sanitary napkin.

FIG. 6 shows sanitary napkin 80 given in FIG. 2 flexed concavely with respect to body facing side 82 of sanitary napkin 80. The folded structures of leakage barriers 33,34 partially unfold to form upstanding walls 84,85 on the body facing side 82 of sanitary napkin 80. The bottom-most layers 86,87 of the pleated cuffs are adhered along their lengths to sanitary napkin 80. The distal ends 31,32,37,38 of leakage barriers 33,34 are anchored entirely to sanitary napkin 80. Consequently, leakage barriers 88,89 are provided by the above structures on flexing of the sanitary napkin.

Returning to FIGS. 3 and 4, when attaching the leakage barriers to the sanitary napkin with adhesive, for example, the folded structure is attached to the sanitary napkin, adhesive is preferably applied along the length of the bottom-most layer 57 in FIG. 3, 62 in FIG. 4, so that only the bottom-most layer is attached to the sanitary napkin allowing the remaining layers to at least partially unfold. If a sanitary napkin with tabs is used, the bottom-most layer can optionally be adhered at least partly or fully to the surface of the tab as shown in FIG. 3.

The sheet that is used to form the leakage barriers may alternatively be made, not separately, but from extensions of perforate cover 43, extensions of the impervious barrier sheet 44, extensions of the materials used to make the tabs 46, combinations of perforate cover 43 and impervious barrier sheet 44, combinations of the materials used to make the tabs 46 and the impervious barrier sheet 44, or combinations of one or more of the foregoing materials.

While the invention has been described and illustrated with reference to specific embodiments, those skilled in the art will recognize that modification and variations may be made without departing from the principles of the invention as described hereinabove and set forth in the following claims. For example, the folded structure may comprise a sheet of material folded in any manner which permits the folded structure to at least partially open when the absorbent product is flexed concavely. Moreover, it is not necessary for the folded structure to extend over the entire length of the leakage barrier. While the leakage barrier preferably traverses the length of the sanitary napkin, the leakage barrier may also preferably need to traverse part of the length of the sanitary napkin such as the central portion of the napkin, either end of the napkin, or any portion of the napkin proximate the fluid discharge. Additionally, the leakage barriers may be attached on the body-facing side of the absorbent product directly adjacent to the edges of the product as shown in the figures or may be attached on the body-facing side of the absorbent product slightly removed from the edges.

I claim:

1. An absorbent product having a central absorbent core, a fluid impervious garment facing side and a fluid pervious body facing side, a first lateral edge, a second lateral edge, a first longitudinal end and a second longitudinal end, the absorbent product comprising:

a first folded structure having a longitudinal shape and a plurality of layers including at least a lower layer and an upper layer, the lower layer being attached longitudinally to the fluid pervious body facing side adjacent the first lateral edge to provide a first leakage barrier; and a second folded structure having a longitudinal shape and a plurality of layers including at least a lower layer and an upper layer, the lower layer being attached longitudinally to the fluid pervious body facing side adjacent the second lateral edge to provide a second leakage barrier; and wherein the first and second leakage barriers have a plurality of folds forming a pleated cuff, the folds being operable to at least partially open to form upstanding walls when the body-facing side is flexed concavely; and wherein each of the first and second leakage barriers has a first distal end and second distal end and wherein the first and second distal ends of each of the leakage barriers are secured to the body-facing side and wherein the plurality of layers are adhered to each other at their respective first and second distal ends to entirely anchor the distal ends of each respective leakage barrier to the absorbent article.

2. The absorbent product of claim 1, wherein each of the leakage barriers has a length substantially equal to the length of the absorbent product.

3. The absorbent product of claim 1, wherein each of the leakage barriers has a length equal to at least one third the length of the absorbent product.

4. The absorbent product of claim 1, wherein each of the first and second leakage barriers comprise a material folded multiple times to form pleated cuffs.

5. The absorbent product of claim 4, wherein the pleated cuffs have top-most layers and bottom-most layers, the bottom-most layers being attached to the fluid pervious body-facing side of the absorbent product.

6. The absorbent product of claim 5, wherein the pleated cuffs are longitudinally shaped and have first and second distal ends, the top-most layer and the bottom-most layer being secured together at the first distal ends and at the second distal ends and attached to the fluid pervious body-facing side of the absorbent product.

7. The absorbent product of claim 6, wherein the first and second ends of the top-most layer and the bottom-most layer are attached longitudinally adjacent to the lateral edge of the body facing side, respectively, proximate the longitudinal ends of the absorbent product.

8. The absorbent product of claim 6, wherein the first and second distal ends of the top-most layer and the bottom-most layer are attached longitudinally adjacent to the lateral edge of the body facing side, respectively, proximate both sides of the central portion of the absorbent product.

9. The absorbent product of claim 6, wherein the first and second distal ends of the top-most layer and the bottom-most layer are attached longitudinally adjacent to the lateral edge of the body facing side, respectively, wherein the first distal end is proximate to one longitudinal end of the absorbent product and the second distal end is proximate to the central portion of the absorbent product.

10. The absorbent product of claim 1, wherein a first tab extends from the first lateral edge of the absorbent product and a second tab extends from the second lateral edge of the absorbent product and wherein the first leakage barrier is attached partly along the first lateral edge and partly on the first tab and the second folded structure is attached partly along the second lateral edge and partly on the second tab.

11. The absorbent product of claim 1, wherein the first and second leakage barriers are formed from a hydrophobic material.

12. The absorbent product of claim 11, wherein the hydrophobic material is selected from the group consisting of nonwovens, plastic films, and foams.

13. The absorbent product of claim 1, wherein the first and second leakage barriers are formed from a hydrophilic material.

14. The absorbent product of claim 13, wherein the hydrophilic material is selected from the group consisting of nonwovens, apertured plastic films and foams.

15. The absorbent product of claim 1, wherein the first and second leakage barriers are formed from a laminated multiple ply sheet having at least one layer of a hydrophobic and at least one layer of a hydrophilic material.

16. The absorbent product of claim 15, wherein the hydrophobic material is selected from the group consisting of nonwovens, plastic films, and foams, and the hydrophilic material is selected from the group consisting of nonwovens, apertured films and foams.

17. The absorbent product of claim 1, wherein the first and second leakage barriers are formed from a hydrophobic, air permeable material.

18. The absorbent product of claim 17, wherein the hydrophobic, air permeable material is selected from the group consisting of nonwovens, apertured plastic films, and foams.

19. The absorbent product of claim 1, wherein the first and second leakage barriers and the fluid impervious garment facing side are formed from the same material.

20. The absorbent product of claim 1, wherein the first and second leakage barriers and the fluid pervious body facing side are formed from the same material.

21. The absorbent product of claim 1, wherein the first and second leakage barriers are formed from materials selected from the group consisting of materials used to make the body facing side and materials used to make the garment facing side, materials used to make side tabs, and combinations thereof.

22. A sanitary napkin comprising a fluid pervious topsheet, a fluid impervious bottom sheet, an absorbent core interposed between the topsheet and the bottom sheet, and first and second lateral edges, and having:

a first longitudinally shaped folded structure having a plurality of layers including at least a lower layer and an upper layer, the lower layer being attached longitudinally to the fluid pervious topsheet adjacent the first lateral edge to provide a first leakage barrier;

a second longitudinally shaped folded structure having a plurality of layers including at least a lower layer and an upper layer, the lower layer being attached longitudinally to the fluid pervious topsheet adjacent the second lateral edge to provide a second leakage barrier; and wherein the first and second leakage barriers have a plurality of folds forming a pleated cuff, the folds being operable to at least partially open to form upstanding walls when the body-facing side is flexed concavely; and wherein each of the first and second leakage barriers has a first distal end and second distal end and wherein the first and second distal ends of each of the leakage barriers are secured to the fluid pervious top sheet and wherein the plurality of layers are adhered to each other at their respective first and second distal ends to entirely anchor the distal ends of each respective leakage barrier to the absorbent article.

23. The sanitary napkin of claim 22, wherein the first and second leakage barriers are longitudinally shaped and have first and second distal ends, the layers of each of the first and second leakage barriers being anchored together at their respective distal ends.

24. The sanitary napkin of claim 22, wherein the first and second leakage barriers comprise a hydrophobic sheet having a plurality of folds forming multiple layered pleated cuffs, the folds being operable to at least partially open to form upstanding walls.

25. The sanitary napkin of claim 24, wherein the upstanding walls substantially prevent side leakage when the sanitary napkin is at least partially bunched between the upstanding walls.

26. The sanitary napkin of claim 24, further comprising:

an absorbent pad disposed between the leakage barriers, the absorbent pad having at least one C-fold formed on opposite edges thereof.

* * * * *